United States Patent [19]
Rivero et al.

[11] Patent Number: 5,492,917
[45] Date of Patent: Feb. 20, 1996

[54] ENDOTHELIN ANTAGONISTS INCORPORATING A CYCLOBUTANE

[75] Inventors: Ralph A. Rivero, Tinton Falls, N.J.; Peter D. Williams, Harleysville; Daniel F. Veber, Ambler, both of Pa.

[73] Assignee: Merck & Co., Inc., Rahway, N.J.

[21] Appl. No.: 128,937

[22] Filed: Sep. 29, 1993

[51] Int. Cl.$^6$ .................. A61K 31/445; A61K 31/21; A61K 31/12; A61K 31/05; C07C 43/20; C07C 33/38; C07C 69/76; C07C 205/00; C07C 49/115; C07C 49/83

[52] U.S. Cl. .................. 514/319; 514/510; 514/532; 514/534; 514/535; 514/539; 514/545; 514/561; 514/562; 514/564; 514/569; 514/617; 514/618; 514/620; 514/621; 514/622; 514/680; 514/712; 514/716; 514/717; 514/718; 514/719; 514/721; 514/727; 514/729; 514/732; 560/10; 560/21; 560/23; 560/24; 560/25; 560/28; 560/52; 560/56; 560/101; 560/102; 564/154; 564/155; 564/157; 564/158; 564/161; 564/162; 564/163; 564/164; 564/165; 564/169; 564/172; 568/31; 568/42; 568/43; 568/56; 568/58; 568/306; 568/326; 568/585; 568/586; 568/632; 568/633; 568/634; 568/659; 568/660; 568/661; 568/662; 568/705; 568/808

[58] Field of Search .................. 546/195; 514/319, 514/510, 532, 534, 535, 539, 545, 561, 562, 564, 618, 619, 620, 621, 712, 716, 717, 718, 567, 569, 617, 627, 689, 727, 729, 732, 719, 721; 568/326, 632, 808, 42, 39, 43, 56, 58, 306, 585, 586, 633, 634, 659, 660, 661, 662, 705; 560/52, 10, 21, 22, 23, 24, 25, 28, 56, 101, 102; 564/165, 169, 172, 154, 155, 157, 158, 161, 162, 163, 164; 562/460, 461, 427, 434, 436

[56] References Cited

FOREIGN PATENT DOCUMENTS

| 2259450 | 9/1991 | United Kingdom. |
| WO92/15321 | 3/1991 | WIPO. |
| 0510526A1 | 4/1991 | WIPO. |

OTHER PUBLICATIONS

Chemical Abstracts, vol. 108, No. 21925, Uno et al., 1987 "Preparation of 1–[Clarlang–and Sulfamoyl)alkyl]–1, 4–diazacycloalkene derivatives as CA antagonists".

Nature, vol. 365, pp. 759–761, 21 Oct. 1993, by Martine Clozel, et al.

Proc. Natl. Acad. Sci. USA, vol. 91, pp. 8052–8056, Aug. 1994, Pharmacology, by E. H. Ohlstein, et al.

The Journal of Pharmacology and Experimental Therapeutics, vol. 271, No. 2, pp. 755–761, 1994, by P. Nambi, et al.

The Journal of Pharmacology and Experimental Therapeutics, vol.271, No. 2, pp. 762–768, 1994, by E. H. Ohlstein, et al.

The Journal of Pharmacology and Experimental Therapeutics, vol. 271, No. 2, pp. 769–775, 1994, by D. P. Brooks, et al.

The Journal of Pharmacology and Experimental Therapeutics, vol. 270, pp. 228–235, 1994, by M. Clozel, et al.

Chemical Abstract, vol. 100 (15) No. 138,708z, Fujiwara et al., 1989, "Studies on synthesis of 10,11–dihydro–5H–debenzy(a,a)cycloheptene derivatives".

Chemical Abstract vol. 91 (3) No. 20181s, Bicherov et al., "Tiberzotrophyin salts" 1979.

Primary Examiner—C. Warren Ivy
Assistant Examiner—Raymond Covington
Attorney, Agent, or Firm—Valerie J. Camara; Mark R. Daniel

[57] ABSTRACT

Novel compounds of the general structural formula I:

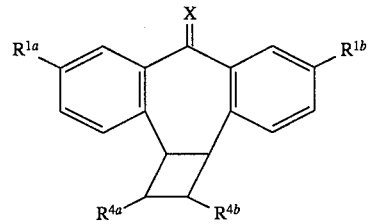

have endothelin antagonist activity and are therefore useful in treating cardiovascular disorders, such as hypertension, pulmonary hypertension, postischemic renal failure, vasospasm, cerebral and cardiac ischemia, myocardial infarction, endotoxic shock, inflammatory diseases including Raynaud's disease and asthma.

15 Claims, No Drawings

ENDOTHELIN ANTAGONISTS INCORPORATING A CYCLOBUTANE

SUMMARY OF THE INVENTION

This invention is concerned with non-peptidic endothelin receptor antagonists and their method of use. The compounds of the present invention are therapeutic agents particularly useful for the treatment of asthma, hypertension, pulmonary hypertension, arteriosclerosis, congestive heart failure, renal failure, particularly post-ischemic renal failure, cyclosporin nephrotoxicity, vasospasm, vascular restenosis, cerebral and cardiac ischemia and other ischemic states, myocardial infarction, Raynaud's disease, the vascular consequences of diabetes such as glaucoma and neuropathy, inflammatory bowel diseases, including Crohn's disease and ulcerative colitis, as well as other inflammatory diseases, or endotoxic shock caused by or associated with endothelin.

BACKGROUND OF THE INVENTION

Endothelin is a 21-amino acid peptide produced by endothelial cells. The peptide is secreted not only by endothelial cells but also by tracheal epithelial cells or from kidney cells. Endothelin (ET-1) has a potent vasoconstrictor effect. The vasoconstricting effect is caused by the binding of endothelin to its receptor on the vascular smooth muscle cells.[1-3]

Endothelin-1 (ET-1) is one of three recently identified potent vasoconstricting peptides which also includes endothelin-2 (ET-2) and endothelin-3 (ET-3) which differ from ET-1 by two and six amino acids, respectively.[4]

Increased levels of endothelin are found in the blood of patients with essential hypertension, acute myocardial infarction, pulmonary hypertension, Raynaud's disease or atherosclerosis or in the washing fluids of the respiratory tract of patients with asthma compared to normal levels.[5-8]

An experimental model of cerebral vasospasm and a second model of acute renal failure have led to the conclusion that endothelin is one of the mediators causing cerebral vasospasm following a subarachnoid hemorrhage, and renal failure.[9-10]

Endothelin was also found to control the release of many physiological substances such as renin, atrial natriuretic peptide, endothelium-derived relaxing factor (EDRF), thromboxane $A_2$,[14], prostacyclin, norepinephrine, angiotensin II and substance p.[11-16] Further, endothelin causes contraction of the smooth muscle of the gastrointestinal tract and the uterine smooth muscle.[17-19] Endothelin has also been shown to promote the growth of rat vascular smooth muscle cells which would suggest a possible relevance to arterial hypertrophy.[20]

Endothelin receptors are present in high concentration in the peripheral tissues and also in the central nervous system, and cerebral administration of endothelin has been shown to induce behavioral changes in animals, suggesting that endothelin may play an important role in controlling neural functions.[21]

Endotoxin has been shown to promote the release of endothelin. This finding has suggested that endothelin is an important mediator for endotoxin-induced diseases.[22-23]

A study has shown that when cyclosporin is added to a renal cell culture endothelin secretion is increased.[24] Another study has shown that administration of cyclosporin to rats led to a decrease in the glomerular filtration rate and an increase in the blood pressure, in association with a remarkable increase in the circulating endothelin level. This cyclosporin-induced renal failure can be suppressed by the administration of anti-endothelin antibody.[25] These studies suggest that endothelin is significantly involved in the pathogenesis of cyclosporin-induced renal disease.

A recent study in patients with congestive heart failure demonstrated a good correlation between the elevated levels of endothelin in the plasma and the severity of the disease.[26]

Substances which specifically inhibit the binding of endothelin to its receptor are believed to block the physiological effects of endothelin and would be useful in treating patients with endothelin related disorders. The present invention discloses potent non-peptidic endothelin antagonists.

Endothelin is an endogenous substance which directly or indirectly (through the controlled release of various other endogenous substances) induces sustained contraction of vascular or non-vascular smooth muscles. Its excess production or excess secretion is believed to be one of the factors responsible for hypertension, pulmonary hypertension, Raynaud's disease, bronchial asthma, acute renal failure, myocardial infarction, angina pectoris, arteriosclerosis, cerebral vasospasm and cerebral infarction.

The novel compounds of the present invention are useful as a non-peptidic endothelin antagonists, and have not been disclosed in any issued patents or patent applications. Fujisawa in European Patent Application EP 457,195, Banyu in EP 436,189 and 460,679, and Takeda in Patent Cooperation Treaty International Publication No. WO 91/13089 have applications disclosing linear and cyclic peptidic compounds as endothelin antagonists. Fujisawa has also disclosed anthraquinone derivatives produced by a fermentation process using Streptomyces sp. No. 89009 in EP 405,421.

A Roussel-Uclaf European Patent Application (EP 498,723) disclosed a series of substituted (1,4-quinolinoxy)methylbiphenylcarboxylic acids as both endothelin antagonists and angiotensin II antagonists. A patent from Hoffmann-La Roche (EP 510,526) has appeared claiming the endothelin antagonist properties of a series of N-(4-pyrimidinyl)benzenesulfonamides and a Smith-Kline Beecham patent application (WO 93/08799) discloses endothelin antagonist properties for a series of indane and indene carboxylic acids.

REFERENCES

1 Nature, 332, 411–415 (1988).
2 FEBS Letters, 231, 440–444 (1988).
3 Biochem. Biophys. Res. Commun. 154, 868–875 (1988).
4 TiPS, 13, 103–108, March 1992.
5 Japan J. Hypertension 12, 79 (1989).
6 J. Vascular Medicine Biology, 2, 207 (1990).
7 J. Am. Med. Association, 264, 2868 (1990).
8 The Lancet, ii, 207 (1990) and The Lancet, ii, 747–748 (1989).
9 Japan. Soc. Cereb. Blood Flow & Metabol. 1, 73 (1989).
10 J. Clin. Invest., 83, 1762–1767 (1989).
11 Biochem. Biophys. Res. Comm. 157, 1164–1168 (1988).
12 Biochem. Biophys. Res. Comm. 155, 167–172 (1989).
13 Proc. Natl. Acad. Sci. USA, 85, 9797–9800 (1989).
14 J. Cardiovasc. Pharmacol., 13, 589–592 (1989).
15 Japan. J. Hypertension 12, 76 (1989).
16 Neuroscience Letters, 102, 179–184 (1989).
17 FEBS Letters, 247, 337–340 (1989).

18 Eur. J. Pharmacol. 154, 227–228 (1988).
19 Biochem. Biophys. Res. Commun., 159, 317–323 (1989).
20 Atherosclerosis, 78, 225–228 (1989).
21 Neuroscience Letters, 97, 276–279 (1989).
22 Biochem. Biophys. Res. Commun. 161, 1220–1227 (1989).
23 Acta. Physiol. Scand., 137, 317–318 (1989).
24 Eur. J. Pharmacol., 180, 191–192 (1990).
25 Kidney Int. 37, 1487–1491 (1990).
26 Mayo Clinic Proc., 67, 719–724 (1992).

DETAILED DESCRIPTION OF THE INVENTION

This invention is concerned with novel compounds of structural Formula I:

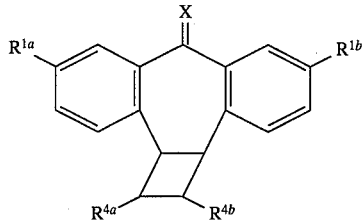

or a pharmaceutically acceptable salt thereof, wherein:

$R^{1a}$ and $R^{1b}$ groups are independently:
(a) H,
(b) halo(F, Cl, Br, I),
(c) $(C_1-C_4)$ alkoxy,
(d) $(C_1-C_5)$ alkyl,
(e) $(C_1-C_5)$ alkylamino,
(f) $(C_1-C_5)$ alkylthio,
(g) $(C_1-C_5)$ perfluoroalkyl,
(h) $SCF_3$,
(i) $NH_2$,
(j) $NHCOR^2$,
(k) $NR^3COR^2$,
(l) $COR^2$,
(m) $NO_2$,
(n) aryl, wherein aryl is defined as phenyl or naphthyl which is unsubstituted or substituted with substituents selected from the group consisting of: halo(F, Cl, Br, I), $(C_1-C_4)$ alkoxy, $(C_1-C_4)$ alkyl, $(C_1-C_4)$ alkylamino, $(C_1-C_4)$ alkylthio, or $(C_1-C_4)$ perfluoroalkyl, or CO-aryl, or
(o) $CH_2$-aryl, wherein aryl is as defined above in $R^1$(n);

$R^2$ is:
(a) halo(F, Cl, Br, I),
(b) $(C_1-C_4)$ alkoxy,
(c) $(C_1-C_5)$ alkyl,
(d) $(C_1-C_5)$ alkylamino,
(e) aryl, wherein aryl is defined as phenyl or naphthyl, which is unsubstituted or substituted with one or two substituents selected from the group consisting of: halo(F, Cl, Br), $(C_1-C_4)$ alkoxy, $(C_1-C_4)$ alkyl, $(C_1-C_4)$ alkylamino, $(C_1-C_4)$ alkylthio, or $(C_1-C_4)$ perfluoroalkyl, or
(f) $CH_2$-aryl, wherein aryl is as defined above in $R^2$(e);

$R^3$ is:
(a) $(C_1-C_5)$ alkyl,
(b) aryl, wherein aryl is defined as phenyl or naphthyl, which is unsubstituted or substituted with one or two substituents selected from the group consisting of: halo(F, Cl, Br), $(C_1-C_4)$ alkoxy, $(C_1-C_4)$ alkyl, $(C_1-C_4)$ alkylthio, or $(C_1-C_4)$ perfluoroalkyl, or (c) $CH_2$-aryl, wherein aryl is as defined above in $R^3$(b);

$R^{4a}$ and $R^{4b}$ groups are independently:
(a) $CH_2OH$,
(b) $CO_2H$,
(c) $CO_2CH_3$,
(d) $CONH_2$,
(e) $CONHR^3$,
(f) $CON(R^3)_2$,

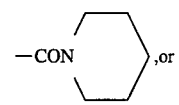

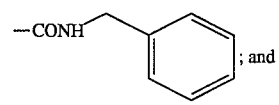

X is:
(a) O,
(b) H, H,
(c) OH, H,
(d) $OR^3$, H, or
(e) $=CHR^3$.

An embodiment of the invention is the compound of structural Formula Ia:

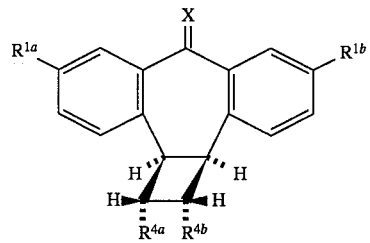

or a pharmaceutically acceptable salt thereof, wherein:

$R^{1a}$ and $R^{1b}$ groups are independently:
(a) H,
(b) halo(F, Cl, Br, I),
(c) $(C_1-C_5)$ alkyl,
(d) $(C_1-C_5)$ perfluoroalkyl,
(e) aryl, wherein aryl is defined as phenyl or naphthyl, which is unsubstituted or substituted with substituents selected from the group consisting of: halo(F, Cl, Br, I), $(C_1-C_4)$ alkoxy, $(C_1-C_4)$ alkyl, $(C_1-C_4)$ alkylamino, $(C_1-C_4)$ alkylthio, or $(C_1-C_4)$ perfluoroalkyl, or CO-aryl, or
(f) $CH2$-aryl, wherein aryl is as defined above in $R^1$(e);

$R^{4a}$ and $R^{4b}$ groups are independently:
(a) $CH_2OH$,
(b) $CO_2H$,
(c) $CO_2CH_3$,
(d) $CONH_2$,
(e) $CONHR^3$,
(f) $CON(R^3)_2$,

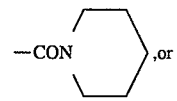

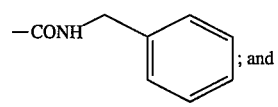

X is:
(a) O,
(b) H, H, (c) OH, H,
(d) OR³, H, or
(e) =CHR³.

A subclass of this embodiment are the compounds of structural Formula Ia:

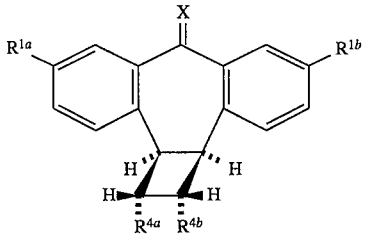

Ia or a pharmaceutically acceptable salt thereof, wherein:

$R^{1a}$ is:
(a) H, or
(b) halo(F, Cl, Br, I);

$R^{1b}$ is:
(a) H,
(b) halo(F, Cl, Br, I),
(c) ($C_1$–$C_5$) alkyl,
(d) ($C_1$–$C_5$) perfluoroalkyl,
(e) aryl, wherein aryl is defined as phenyl, 2-anisyl, 3-anisyl, 4-anisyl, 3,5-ditrifluoromethylphenyl, 2,4-ditrifluoromethylphenyl, 4-ethylphenyl, 2-tolyl, 3-tolyl, 4-tolyl, 2-chlorophenyl, 3-chlorophenyl, 4-chlorophenyl, 2,4-dichlorophenyl, 3,5-dichlorophenyl, 1-naphthyl, or 2-naphthyl, or
(f) $CH_2$-aryl, wherein aryl is as defined above in $R^1$(e);

$R^{4a}$ and $R^{4b}$ groups are independently:
(a) $CH_2OH$,
(b) $CO_2H$, or
(c) $CO_2CH_3$; and X is:
(a) O,
(b) H, H,
(c) OH, H,
(d) OR³, H, or
(e) =CHR³.

Table I further exemplifies the scope of the invention described by Formula Ia:

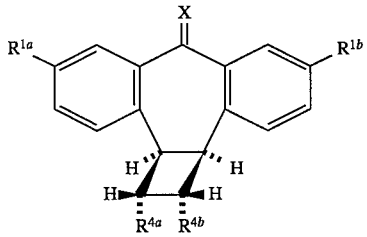

Ia wherein the substituents are as defined in the table below:

| Example # | X | $R^{1a}$, $R^{1b}$ | $R^{4a}$, $R^{4b}$ |
|---|---|---|---|
| 6 | O | H,1-naphthyl | $CO_2H,CO_2H$ |
| 7 | O | H,4-anisyl | $CO_2H,CO_2H$ |
| 8 | O | H,2-anisyl | $CO_2H,CO_2H$ |
| 9 | O | H,3-anisyl | $CO_2H,CO_2H$ |
| 10 | O | H,(3,5-ditrifluoromethyl)phenyl | $CO_2H,CO_2H$ |
| 11 | O | H,4-ethylphenyl | $CO_2H,CO_2H$ |
| 12 | O | H,4-tolyl | $CO_2H,CO_2H$ |
| 13 | O | H,(2,4-dichloro)phenyl | $CO_2H,CO_2H$ |
| 14 | O | H,(3,5-dichloro)phenyl | $CO_2H,CO_2H$ |

-continued

| Example # | X | $R^{1a}$, $R^{1b}$ | $R^{4a}$, $R^{4b}$ |
|---|---|---|---|
| 15 | O | H,4-chlorophenyl | $CO_2H,CO_2H$ |
| 16 | O | H,2-tolyl | $CO_2H,CO_2H$ |
| 1 | O | H,Br | $CO_2H,CO_2H$ |
| 3 | O | H,H | $CO_2H,CO_2H$ |
| 4 | O | H,phenyl | $CO_2H,CO_2H$ |
| 2 | O | Br,Br | $CO_2H,CO_2H$ |
| 5 | H,OH | H,H | $CH_2OH,CH_2OH$. |

An embodiment of the invention is the compound of structural Formula Ia:

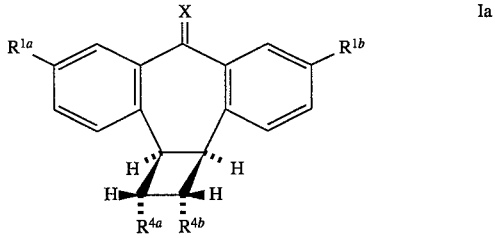

Ia or a pharmaceutically acceptable salt thereof, wherein:

$R^{1a}$ and $R^{1b}$ groups are: H; and
$R^{4a}$ and $R^{4b}$ groups are independently:
(a) $CO_2H$,
(b) $CONH_2$,
(c) $CONHR^3$,
(d) $CON(R^3)_2$,

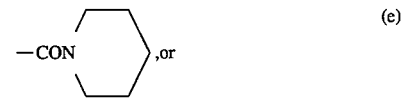

(e)

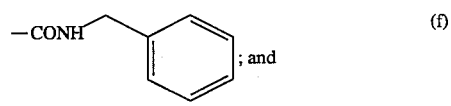

(f)

; and

X is: O.

Table I further exemplifies the scope of the invention described by Formula Ia:

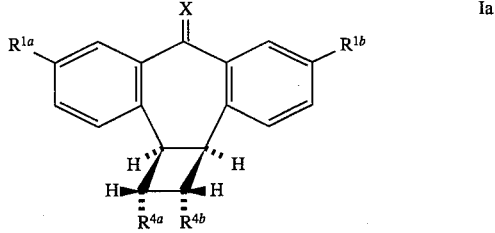

Ia wherein the substituents are as defined in the table below:

| Example # | X | $R^{1a}$,$R^{1b}$ | $R^{4a}$,$R^{4b}$ |
|---|---|---|---|
| 17 | O | H,H | $CO_2H$,$CONH_2$ |
| — | O | H,H | $CONH_2$,$CO_2H$ |
| 18 | O | H,H | $CO_2H$, —CON⟨⟩ |
| — | O | H,H | —CON⟨⟩, $CO_2H$, |

-continued

| Example # | X | $R^{1a},R^{1b}$ | $R^{4a},R^{4b}$ |
|---|---|---|---|
| 19 | O | H,H | $CO_2H$, $-CONH-CH_2-C_6H_5$ |
| — | O | H,H | $-CONH-CH_2-C_6H_5$, $CO_2H$ |

The alkyl substituents recited above denote straight and branched chain hydrocarbons of the length specified such as methyl, ethyl, isopropyl, isobutyl, neopentyl, isopentyl, etc.

The alkenyl substituents denote alkyl groups as described above which are modified so that each contains a carbon to carbon double bond such as vinyl, allyl and 2-butenyl.

Cycloalkyl denotes tings composed of 3 to 8 methylene groups, each of which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl or carbazolyl.

Although the reaction schemes described below are reasonably general, it will be understood by those skilled in the art of organic synthesis that one or more functional groups present in a given compound of Formula I may render the molecule incompatible with a particular synthetic sequence. In such a case an alternative synthetic route, an altered order of steps, or a strategy of functional group protection (see: Greene T. W. *Protective Groups in Organic Synthesis*; John Wiley & Sons; New York, 1981) and deprotection may be employed. In all cases the particular reaction conditions, including reagents, solvent, temperature and time, should be chosen so that they are consistent with the nature of the functionality present in the molecule.

The compounds of Formula I can be synthesized using the reactions and techniques illustrated in the following schemes and described below. Some of the reaction schemes described here have been generalized for simplicity, and it is to be understood that in these generalized schemes, unless specified more narrowly in the text, the alkyl and aryl groups represent unfunctionalized or functionalized derivatives as described before.

The general procedure for the synthesis of 4"-aryl-substituted 8,9-dicarboxydibenzo[2,3:5,6]bicyclo[5.2.0]nonan-4-ones is illustrated in scheme I. Bromination of o-phenethylbenzoic acid in sulfur dioxide in the presence of TFA provides the desired product 2-(p-bromophenethyl)-benzoic acid (Ib). Cyclization to the desired dibenzosuberone Ic can be accomplished by heating benzoic acid derivative Ib in neat polyphosphoric acid or, alternatively the acid chloride, prepared using thionyl chloride, can be treated with $AlCl_3$ in $CH_2Cl_2$. Treatment of Ic with NBS and AIBN or benzoylperoxide in refluxing $CCl_4$ followed by elimination of the newly added bromide with triethylamine affords the desired dibenzosuberenone derivative Id. Photolysis of Id with an excess of maleic anhydride in toluene in a Rayonet reactor irradiating with 300 nanometer tubes or with a Hanovia medium pressure Hg lamp with a pyrex filter provides, after hydrolysis with NaOH and purification, the desired diacid derivative Ie. Further elaboration of the 4"-position can be carded out by coupling of Ie with a variety of aryl boronic acid derivatives and tin reagents.

Scheme I

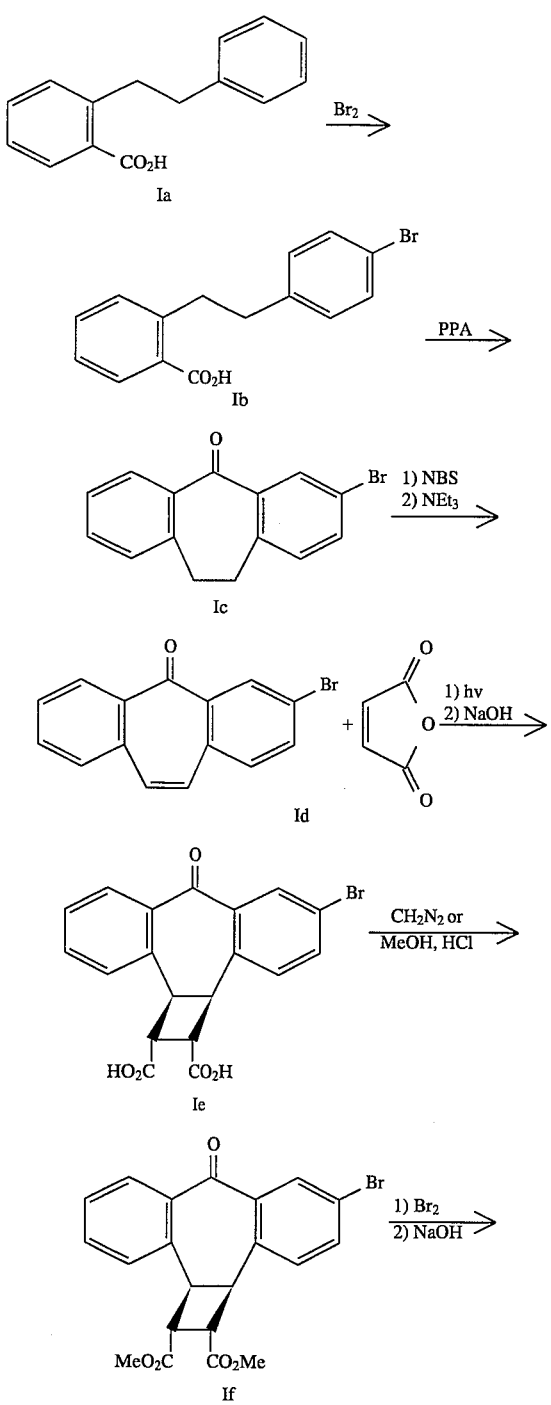

-continued
Scheme I

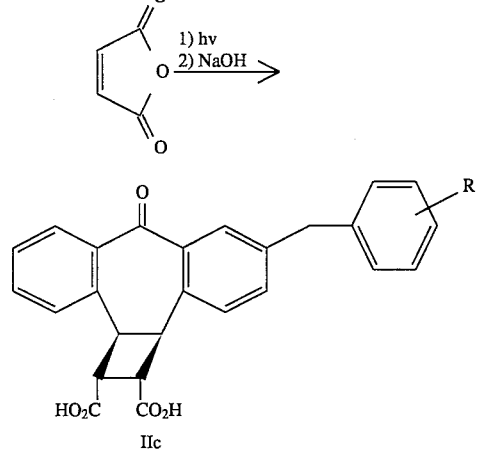

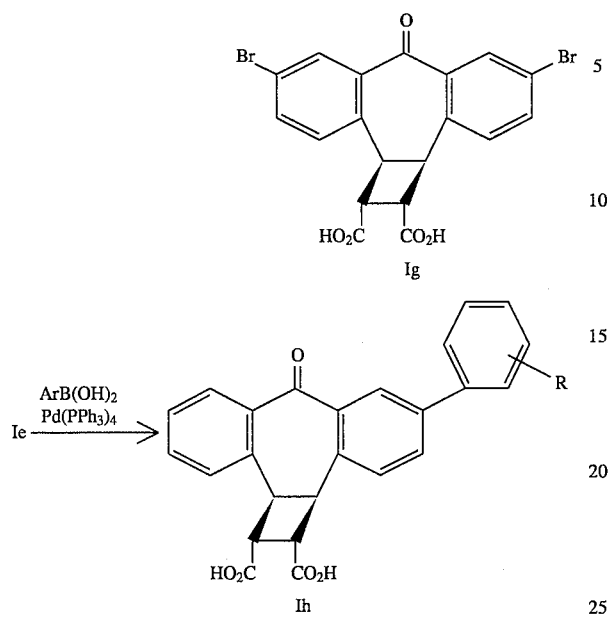

The general procedure for the synthesis of 4"-benzyl-substituted 8,9-dicarboxydi-benzo[2,3:5,6]bicyclo[5.2.0]nonan-4-ones is illustrated in scheme II. Reaction of Id with tetramethyltin provides dibenzosuberenone IIa. NBS bromination followed by palladium catalyzed boronic acid coupling provides derivatives IIb. Photolysis of IIb with an excess of maleic anhydride in toluene in a Rayonet reactor irradiating with 300 nanometer tubes or with a Hanovia medium pressure Hg lamp with a pyrex filter provides, after hydrolysis with NaOH and purification, the desired diacid derivative IIc.

Scheme II

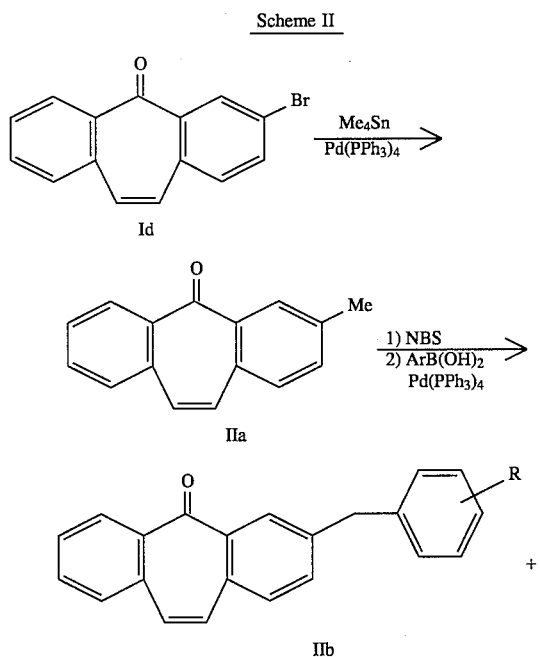

-continued
Scheme II

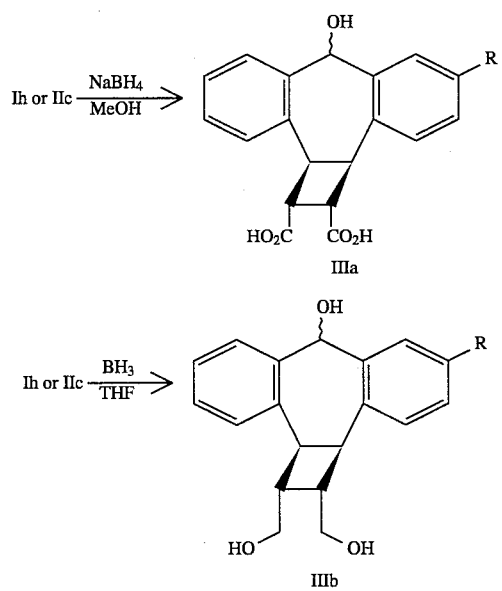

The general procedure for the synthesis of 4"-substituted 8,9-dicarboxydibenzo[2,3:5,6]bicyclo[5.2.0]nonan-4-ols and 4"-substituted 8,9-dihydroxymethyldibenzo[2,3:5,6]bicyclo[5.2.0]nonan-4-ols is illustrated in scheme HI. Reaction of Ih or IIc with $NaBH_4$ in MeOH provides diastereomeric alcohols IIIa. Reaction of Ih or IIc with borane in THF provides triols IIIb.

Scheme III

The reactions described in the preceding section are performed in solvents appropriate to the reagents and materials employed and suitable for the transformation being effected. It is understood by those skilled in the art of organic synthesis that the functionality present in the substrate and in the reagents being employed should be consistent with the chemical transformations being conducted. Depending upon the reactions and techniques employed, optimal yields may require changing the order of synthetic steps or use of protecting groups followed by deprotection.

The novel compounds of general Formula I described here which are useful in the treatment of diseases caused by or associated with the peptide hormone endothelin form salts with various inorganic and organic acids and bases and these salts are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2S O_4$, $H_3PO_4$, methanesulfonic, toluenesulfonic, maleic, fumaric, camphorsulfonic.

The salts can be formed by conventional means, such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be appreciated that the compounds of general Formula I in this invention may be derivatised at functional groups to provide prodrug derivatives which are capable of conversion back to the parent compounds in vivo. The concept of prodrug administration has been extensively reviewed (e.g. A. A. Sinkula in Annual Reports in Medicinal Chemistry, Vol 10, R. V. Heinzelman, Ed., Academic Press, New York, 1975, Ch. 31, pp. 306–326, H. Ferres *Drugs of Today,* 1983,19, 499 and *J. Med. Chem.,* 1975, 18, 172). Examples of such prodrugs include the physiologically acceptable and metabolically labile ester derivatives, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formula I, similar to the metabolically labile esters, which are capable of producing the parent compounds of general Formula I in vivo, are within the scope of this invention.

It will be further appreciated that the majority of compounds of general Formula I claimed herein are asymmetric and unless otherwise stated, are produced as racemic mixtures of enantiomers and that both the racemic compounds and the resolved individual enantiomers are considered to be in the scope of this invention. The racemic compounds of this invention may be resolved to provide individual enantiomers utilizing methods known to those skilled in the art of organic synthesis. For example, diastereoisomeric salts, esters or imides may be obtained from a racemic compound of general Formula I and a suitable optically active amine, amino acid, alcohol or the like. The diastereoisomeric salts, esters or imides are separated and purified, the optically active enantiomers are regenerated and the preferred enantiomer is the more potent isomer. The resolved enantiomers of the compounds of general Formula I, their pharmaceutically acceptable salts and their prodrug forms are also included within the scope of this invention.

The novel compounds of Formula I disclosed in this invention which are synthesized according to the methods and techniques described in the preceding Schemes, are potent receptor antagonists of the peptide hormone endothelin. Thus, these compounds have therapeutic usefulness in preventing, decreasing or modulating the various physiological effects of endothelin discussed above, by wholly or partially blocking access of endothelin to its receptor.

The biological activity of the novel compounds of Formula I disclosed in this invention may be demonstrated using the following assay protocols.

Endothelin Receptor Binding Assays

The binding of the novel compounds of this invention to the endothelin receptor was determined in accordance with the assay described in detail immediately below. It is similar to the assay described in Ambar et al. (1989) *Biochem. Biophys. Res. Commun.* 158, 195–201; and Kloog et al. (1989) *FEBS Letters,* 253, 199–202.

The endothelins (ETs) have a number of potent effects on a variety of cells, and exert their action by interacting with specific receptors present on cell membranes. The compounds described in the present invention act as antagonists of ET at the receptors. In order to identify ET antagonists and determine their efficacy in vitro, the following three ligand receptor assays were established.

Receptor Binding Assay Using Cow Aorta Membrane Preparation

Thoracic aortae were obtained from freshly slaughtered calves and brought to the lab on wet ice. The adventitia were removed, and the aorta was opened up lengthwise. The lumenal surface of the tissue was scrubbed with cheesecloth to remove the endothelial layer. The tissue was ground in a meat grinder, and suspended in ice-cold 0.25M sucrose, 5 mM tris-HCl, pH 7.4, containing 0.5 mg/mL leupeptin and 7 mg/mL pepstatin A. Tissue was homogenized twice and then centrifuged for 10 minutes at 750×g at 4° C. The supernatant was filtered through cheesecloth and centrifuged again for 30 minutes at 48,000×g at 4° C. The pellet thus obtained was resuspended in the buffer solution described above (including the protease inhibitors), and aliquots were quick-frozen and stored at −70° C. until use. Membranes were diluted into 50 mM KPi, 5 mM EDTA pH 7.5 containing 0.01% human serum albumin. Assays were done in triplicate. Test compounds and 100 pM [$^{125}$I]-endothelin-1 (2000–2200 Ci/mmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 is measured in the presence of 100 nM unlabelled endothelin-1 [Endothelin-i (ET-1) was purchased from Peptides International (Louisville, KY)]. Specific binding is total binding minus nondisplaceable binding. The inhibitory concentration ($IC_{50}$) which gives 50% displacement of the total specifically bound [$^{125}$I]-endothelin-1 was presented as a measure of the efficacy of such compounds as ET antagonists.

Receptor Binding Assay Using Rat Hippocampal Membrane Preparation

Rat hippocampi were obtained from freshly sacrificed male Sprague-Dawley rats and placed in ice cold 0.25M sucrose, 5 mM tris-HCl, pH 7.4 containing 0.5 mg/mL leupeptin, 7 mg/mL pepstatin A. Hippocampi were weighed and placed in a Dounce homogenizer with 25 volumes (wet weight to volume) ice-cold sucrose buffer in the presence of protease inhibitors. Hippocampi were homogenized using a Dounce (glass-glass) homogenizer with type A pestle, with homogenizer in ice. Tissue homogenate was centrifuged at 750×g for 10 min at 4° C. Supernatant was filtered through dampened cheesecloth, and centrifuged again at 48,000×g for 30 min at 4° C. Pellets were resuspended in sucrose buffer with protease inhibitors. Aliquots of this preparation were quick frozen and stored at −70° C. until use. Membranes were diluted into 50 mM KPi, 5 mM EDTA pH 7.5 containing 0.01% human serum albumin. Assays were done in triplicate. Test compounds and 25 pM [$^{125}$I]-endothelin-1 (2000–2200 Ci/mmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$i]-endothelin-1 is measured in the presence of 100 nM unlabelled endothelin-1. Specific binding is total binding minus nondisplaceable binding. The inhibitory concentration (IC$_{50}$) which gives 50% displacement of the total specifically bound [$^{125}$I]-endothelin-1 was presented as a measure of the efficacy of such compounds as endothelin antagonists.

Receptor Binding Assay Using Cloned Human ET Receptors Expressed in Chinese Hamster Ovary Cells Both endothelin receptor subtypes were cloned from a human cDNA library and were individually expressed in Chinese Hamster Ovary cells. Cells were harvested by addition of 126 mM NaCl, 5 mM KCl, 2 mM EDTA, 1 mM NaH$_2$PO$_4$, 15 mM glucose, 10 mM tris/HEPES pH 7.4 Cells were centrifuged at 250×g for 5 minutes. The supernatant was aspirated off, and the cells were resuspended in the 50 mM KPi, 5 mM EDTA pH 7.5 containing 0.01% human serum albumin. Assays were done in triplicate. Test compounds and 25–100 pM [$^{125}$I]-endothelin-1 (2000–2200 Ci/mmole, obtained from New England Nuclear or Amersham) were placed in a tube containing 50 mM KPi, 5 mM EDTA pH 7.5 containing 0.01% human serum albumin, and the cells prepared above were added last. The samples were incubated for 60 min at 37° C. At the end of this incubation, samples were filtered onto prewetted (with 2% BSA in water) glass fiber filter pads and washed with 150 mM NaCl, 0.1% BSA.

The filters were assayed for $^{125}$I radioactivity in a gamma counter. Nondisplaceable binding of [$^{125}$I]-endothelin-1 is measured in the presence of 100 nM unlabelled endothelin-1. Specific binding is total binding minus nondisplaceable binding. The inhibitory concentration (IC$_{50}$) which gives 50% displacement of the total specifically bound [$^{125}$I]-endothelin-1 was presented as a measure of the efficacy of such compounds as endothelin antagonists.

The binding assays described above were used to evaluate the potency of interaction of representative compounds of the invention with endothelin receptors. To determine whether these compounds were endothelin antagonists, assays which measure the ability of the compounds to inhibit endothelin-stimulated phosphatidylinositol hydrolysis were established. Rat uterus contains predominantly one of the known endothelin receptor subtypes (ET$_A$).

Phosphatidylinositol Hydrolysis Assays Using Rat Uterine Slices

Diethylstilbestrol primed female Sprague-Dawley rats were sacrificed and their uteri were collected, dissected of fat and connective tissue and minced. Minced tissue was added to oxygenated (95% O$_2$, 5% CO$_2$) 127 mM NaCl, 25 mM NaHCO$_3$, 10 mM Glucose, 2.5 mM KCl, 1.2 mM KH$_2$PO$_4$, 1.2 mM MgSO$_4$, 1.8 mM CalC$_2$. To the tissue mince, 1.2 mM myo-[$^3$H]-inositol (Amersham) was added. The mince was incubated 90 min at 37° C, with constant oxygenation. After incubation, the loaded tissue mince was washed five times with the same oxygenated buffer to remove excess radiolabelled inositol. The tissue mince was resuspended in the above buffer, containing 10 mM LiCl, aliquotted into tubes, and 3 nM endothelin-1 with and without test compounds was added to start the assay. Assays were done in quadruplicate. Samples were incubated at 37° C. under blowing O$_2$ in a hooded water bath for 30 minutes. Reaction was stopped by addition of trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration (IC$_{50}$) is the concentration of test compound required to give a sample activity of 50% of control value.

Sarafotoxin S6c is a member of the endothelin family which binds preferentially to one of the known endothelin receptor subtypes (ET$_B$).

Phosphatidylinositol Hydrolysis Assays Using Rat Lung Slices

Male Sprague-Dawley rats were sacrificed and their lungs were collected, dissected of fat and connective tissue and minced. Minced tissue was added to oxygenated (95% O$_2$, 5% CO$_2$) 127 mM NaCl, 25 mM NaHCO$_3$, 10 mM glucose, 2.5 mM KCl, 1.2 mM KH$_2$PO$_4$, 1.2 mM MgSO$_4$, 1.8 mM CaCl. To the tissue mince, 1.2 pM myo-[$^3$H]-inositol was added. The mince was incubated 60 min at 37° C., with constant oxygenation. After incubation, loaded tissue mince was washed five times with the same oxygenated buffer to remove excess radiolabelled inositol. Tissue mince was resuspended in the above buffer, containing 10 mM LiCl, aliquotted into tubes, and 3 nM sarafotoxin S6c with and without test compounds was added to start the assay. Assays were done in quadruplicate. Samples were incubated at 37° C. under blowing O$_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of sarafotoxin minus the values in the absence of sarafotoxin (basal). Test sample values are the values in the presence of sarafotoxin and test sample minus basal. Inhibitory concentration ($IC_{50}$) is the concentration of test compound required to give a sample activity of 50% of control value.

Phosphatidylinositol Hydrolysis Assays Using Cloned Human Endothelin Receptors Expressed in Chinese Hamster Ovary Cells Endothelin receptors of both receptor subtypes were cloned from a human cDNA library and were individually expressed in Chinese Hamster Ovary cells. Cells were loaded overnight by the addition of 1.2 pM myo-[$^3$H]-inositol to their growth medium. Cells were harvested by addition of 126 mM NaCl, 5 mM KCl, 2 mM EDTA, 1 mM $NaH_2PO_4$, 15 mM glucose, 10 mM tris/HEPES pH 7.4. Cells were washed five times by centrifugation at 250×g for 5 minutes to remove excess radiolabelled inositol. The supernatant was aspirated off, and the cells were resuspended in the same oxygenated (95% $O_2$, 5% $CO_2$) buffer containing 10 mM LiCl, aliquotted into tubes, and 0.3 nM endothelin-1 with and without test compounds was added to start the assay. Assays were done in quadruplicate. Samples were incubated at 37° C. under blowing $O_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration ($IC_{50}$) is the concentration of test compound required to give a sample activity of 50% of control value.

Using the methodology described above, representative compounds of the invention were evaluated and found to exhibit $IC_{50}$ values of at least <50 µM thereby demonstrating and continuing the utility of the compounds of the invention as effective endothelin antagonists.

Endothelin (ET-1), and two closely related bioactive peptides, ET-2 and ET-3, are widely distributed in mammalian tissues, and they can induce numerous biological responses in non-vascular as well as vascular tissues by binding to at least two distinct endothelin receptor subtypes. In addition to cardiovascular smooth muscle, neural and atrial sites, endothelin receptors may also be found in gastrointestinal, kidney, lung, urogenital, uteral and placental tissues. Endothelin is a potent vasoconstrictor peptide and thus plays a role in arterial pressure-volume homeostasis. Peripheral and coronary vascular resistance is increased by endothelin, cardiac output is decreased, and plasma renin activity is increased. Endothelin causes a reduction in renal blood flow and glomerular filtration rate, while levels of atrial natriuretic factor, vasopressin, and aldosterone become elevated.

Accordingly the novel compounds of the present invention are useful in human therapy for treating asthma, hypertension, renal failure particularly post-ischemic renal failure, cyclosporin nephrotoxicity, vasospasm, cerebral and cardiac ischemia, myocardial infarction, or endotoxin shock caused by or associated with endothelin, by administration to a patient in need of such treatment of a therapeutically effective amount thereof.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 0.5 mg to 1.0 g. per patient per day which can be administered in single or multiple doses. Perferably, the dosage range will be about 0.5 mg to 500 mg. per patient per day; more preferably about 0.5 mg to 200 mg. per patient per day.

It is also considered, in accordance with the present invention, that antagonists for the endothelin receptor may be useful in preventing or reducing restenosis subsequent to denudation following angioplasty. Denudation results in myointimal thickening following angioplasty, due to increased endothelin release. Endothelin acts as a growth factor with respect to smooth muscle and fibroblastic cells, and possibly other types of cells. Endothelin is also a neuropeptide, acting on the posterior pituitary, where it modulates the release of the neurosecretory hormones vasopressin and oxytocin. Endothelin released from the posterior pituitary also acts as a circulating hormone, having a wide range of actions as discussed further above. This includes effects on the endocrine system, especially the adrenal glands. Endothelin increases plasma levels of epinephrine.

The present invention also relates to pharmaceutical compositions for treating asthma, hypertension, renal failure, particularly post-ischemic renal failure, the vascular consequences of diabetes such as glaucoma and neuropathy, cyclosporin nephrotoxicity, vasospasm, cerebral and cardiac ischemia, myocardial infarction, or endotoxin shock caused by or associated with endothelin, comprising a therapeutically effective amount of the novel compound of this invention together with a pharmaceutically acceptable carrier therefor.

About 0.5 mg to 1.0 g. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage uniform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of Formula I and their incorporation into pharmaceutical compositions and as such are not to be considered as limiting the invention set forth in the claims appended hereto.

EXAMPLE 1

4"-bromo-8,9-dicarboxydibenzo[2,3:5,6]bicyclo[5.2.0]nonan-4-one (compound Ie of scheme I).
Step A: Preparation of 2-(p-bromophenethyl)benzoic acid (compound Ib of scheme I).

Sulfur dioxide (625 mL) was condensed into a large flask with a dry ice condenser to this flask was added TFA (10 mL) and bromine (2 equiv). When the solution temperature reached −50°, o-phenethylbenzoic acid was added. The reaction was stirred at −28° C. for 17 hours. The $SO_2$ and excess bromine were evaporated off at room temperature over a 2 hour period leaving slightly yellow solid. A 30 g sample was dissolved in hot toluene-hexane (100 mL of 2:3) with a few mL of $Et_2O$. The solution was cooled slowly to 10° C., and the product was isolated by filtration.
Step B: Preparation of 2-bromo-dibenzosuberone (compound Ic of scheme I).

To a solution of the product of step A in $CH_2Cl_2$ was added thionyl chloride (20 fold excess) and several drops of DMF. After stirring at room temperature for 4 hours, the solvent was removed under reduced pressure. The residue was dissolved in $CH_2Cl_2$ and this new solution was added to a stirred suspension of $AlCl_3$ (2.2 equiv) in $CH_2Cl_2$ at 5° C. The reaction was stirred for 1.5 hours at 0°–5° C. With continued cooling the reaction was quenched carefully with $H_2O$. The $CH_2Cl_2$ layer was separated and the aqueous layer extracted with $CH_2Cl_2$. The combined extracts were dried over $MgSO_4$ and filtered to provide the titled compound.

$^1H$ NMR (400 MHz, $CDCl_3$) δ3.17 (m, 4H), 7.09 (d, 1H), 7.20 (d, 1H), 7.32 (dt, 1H), 7.43 (dt, 1H), 7.51 (dd, 1H), 7.97 (dd, 1H), 8.12 (d, 1H).
Step C: Preparation of 2-bromo-dibenzosubereneone (compound Id of scheme I).

To a solution of the product of step B (5.63 g, 19.6 mmol) in dry $CCl_4$ (70 mL) was added NBS (3.84 g, 1.1 equiv) and a catalytic amount of AIBN. The reaction was stirred at reflux under $N_2$ for 3 hours. To the mixture was added $NEt_3$ and the reaction was stirred at reflux for 4 hours. After cooling to room temperature the reaction was diluted with EtOAc/$Et_2O$ and the organic was washed with 2N HCl, $H_2O$ and brine. The organic was dried over $MgSO_4$ and concentrated in vacuo. The titled compound, Rf=0.65 (6:1 hex/EtOAc, 2×'s), was purified by crystallization from $Et_2O$/hex.

$^1H$ NMR (200 MHz, $CDCl_3$) δ7.00 (q, 2H), 7.37 (d, 1H), 7.50–7.75 (comp m, 4H), 8.20 (d, 1H), 8.36 (d, 1H).
Step D: Preparation of 4"-bromo-8,9-dicarboxydibenzo[2,3:5,6]-bicyclo[5.2.0]nonan-4-one (compound Ie of scheme I).

A solution of the product of step C (1.8 g, 6.32 mmol) and maleic anhydride (6.2 g, 63.2 mmol) in toluene (300 mL) and 1,4dioxane (50 mL) was irradiated with a 450 watt medium pressure Hg lamp with a pyrex filter for 24 hours. The next day the solvent was removed and the residue was disssolved in THF (100 mL) and 2N NaOH (79 mL) was added. The mixture was stirred at room temperature for 2.5 hours. The THF was removed and the remaining aqueous was extracted with EtOAc. The aqueous was acidified to ca. pH 3 with solid citric acid and extracted with EtOAc several times. The second EtOAc extraction containing the titled compound was dried over anhydrous $MgSO_4$ and concentrated in vacuo. The titled compound, retention time=5.15 min. (55:45 $CH_3CN/H_2O$, 0.1% TFA, 1 mL/min, C18 Dynamax analytical column), was purified by reverse phase MPLC on a RP 8 column eluting with 2:1 $H_2O/CH_3CN$, 0.1% TFA at 2 mL/min.

$^1H$ NMR (400 MHz, $CD_3OD$) δ3.36 (m, 2H), 4.43 (d, 1H), 7.24 (d, 1H), 7.32 (d, 1H), 7.38 (dt, 1H), 7.53 (dt, 1H), 7.61 (dd, 1H), 7.64 (dd, 1H), 7.71 (d, 1H).

EXAMPLE 2

4',4"-dibromo-8,9-dicarboxydibenzo[2,3:5,6]bicyclo[5.2.0]nonan-4-one (compound Ig of scheme I).
Step A: Preparation 8,9-dimethoxycarboxydibenzo[2,3:5,6]-bicyclo[5.2.0]nonan-4-one Commercially available dibenzosubereneone was photolyzed s with maleic anhydride using the conditions described in step D, of example 1. The crude diacid product was treated with MeOH (40 mL) and acetyl chloride (2 mL) to afford the titled compound Rf=0.35 (3:1 hex/EtOac) after removal of volatiles. The titled compound was purified by flash chromatography eluting with 5:1 hex/EtOAc.

$^1H$ NMR (200 MHz, $CDCl_3$) δ3.42 (m, 2H), 3.71 (s, 6H), 4.48 (m, 2H), 7.23 (dd, 2H), 7.31 (dt, 2H), 7.45 (dt, 2H), 7.67 (dd, 2H).
Step B: Preparation 4',4"-dibromo-8,9-dimethoxycarboxydibenzo-[2,3:5,6]bicyclo[5.2.0]nonan-4-one To a solution of the product of step A (135 mg, 0.42 mmol) in $CH_2Cl_2$ cooled to 0° C. was added $AgO_2CCF_3$ (213 mg, 2.3 equiv) and $Br_2$ (0.048 mL, 2.1 equiv). The reaction was warmed to room temperature and stirred for 2 hours. The solid was removed by filtration and the filtrated was concentrated in vacuo. The titled compound, Rf=0.28 (2:1 hex/EtOAc), was purified by radial chromatography eluting with 4.5:1 hex/EtOAc.

$^1H$ NMR (400 MHz, $CDCl_3$) δ3.32 (m, 2H), 3.64 (s, 6H), 4.32 (m, 2H), 7.08 (d, 2H), 7.53 (dd, 2H), 7.69 (d, 2H).
Step C: Preparation of 4',4"-dibromo-8,9-dicarboxydibenzo[2,3:5,6]bicyclo[5.2.0]nonan-4-one (compound If of scheme I)

To a solution of the product of step B (44 mg, 0.087 mmol) in MeOH (5 mL) was added 2N NaOH until the solution turned slightly cloudy. After 3 hours the solvent was removed and the remaining aqueous was acidified and extracted with EtOAc. The organic was washed with brine, dried over $MgSO_4$ and concentrated in vacuo to provide the titled compound.

$^1$H NMR (400 MHz, CD$_3$OD) δ3.31 (m, 2H), 4.42 (m, 2H), 7.25 (d, 2H), 7.67 (dd, 2H), 7.73 (d, 2H).

EXAMPLE 3

8,9-dicarboxydibenzo[2,3:5,6]bicyclo[5.2.0]nonan-4-one (desbromo-compound If of scheme I).

To a solution of the product step A, Example 2 in MeOH (2 mL) was added 2N NaOH until the mixture remained cloudy. After 3 hours the solvent was removed and the aqueous was acidified to pH 2 and extracted with EtOAc. The organic was washed with brine, dried over MgSO$_4$ and concentrated in vacuo to provide the titled compound.

$^1$H NMR (400 MHz, CD$_3$OD) δ3.29 (m, 2H), 4.43 (m, 2H), 7.31 (d, 2H), 7.34 (dr, 2H), 7.48 (dr, 2H), 7.57 (dr, 2H).

EXAMPLE 4

4"-phenyl-8,9-dicarboxydibenzo[2,3:5,6]bicyclo[5.2.0] nonan-4-one (compound Ih of scheme I, where Ar=Ph).

To a solution of the product of step D, Example 1, (15 mg, 0.037 mmol) and phenylboronic acid (14 rag, 3 equiv) in toluene (2 mL) and EtOH (1 mL) was added Pd(PPh$_3$)$_4$ (7 mg) and 1.25N NaOH (0.25 mL). The reaction was stirred at 100° C. for 3 hours. The reaction was cooled to ambient temperature and extracted with Et$_2$O and the aqueous was acidified to pH 2 and extracted with EtOAc. The EtOAc extract was washed with H$_2$O and brine and dried over MgSO$_4$. The solvent was removed and the titled compound, retention time=6.58 min. (55:45 CH$_3$CN/H$_2$O, 0.1% TFA, 1 mL/min, C18 Dynamax analytical column), was purified by trimration from Et$_2$O/hex.

$^1$H NMR (400 MHz, CDCl$_3$) δ3.36 (m, 2H), 4.48 (m, 2H), 7.28–7.41 (comp m, 4H), 7.43 (d, 1H), 7.50 (dd, 1H), 7.53–7.62 (comp m, 4H), 7.77 (dd, 1H), 7.81 (d, 1H).

EXAMPLE 5

8,9-dihydroxymethyldibenzo[2,3:5,6]bicyclo[5.2.0]nonan-4-ol

To a solution of the product of Example 3 (100 mg, 0.31 mmol) in dry THF (15 mL) was added 1.0M BH$_3$.THF(4 equiv., 1.4 mmol). The solution was warmed to room temperature for 1 hr. and then the solvent was removed in vacuo. The residue was dissolved in CHCl$_3$ and extracted with 1N NaOH. The chloroform layer was separated and dried over sodium sulfate. The chloroform solution was filtered from the sodium sulfate and the chloroform was removed in vacuo. High pressure liquid chromatograph of the crude product indicated a new major peak with a renttion time of 6.52 minutes. The diacid starting material having a retention time of 7.28 minutes. The residue was triturated in ether and filtered to give about 50 mg of a white solid (RT=6.52 minutes, 97% pure).

Examples 6 through 16, illustrated in Table I, were prepared by coupling 4"-bromo-8,9-dicarboxydibenzo[2,3:5,6]bicyclo[5.2.0]nonan-4-one (Example 1) with the boronic acid derivative shown using the procedure described in example 4. Any variations to the procedure are described in the 'comments' column.

TABLE I

| Ex | ArB(OH)$_2$ | Retention time# | Comments |
|---|---|---|---|
| 6 | 1-naphthylB(OH)$_2$ | 11.06 | RP-8 MPLC purification |
| 7 | (4-MeO)phenylB(OH)$_2$ | 6.06 | tritutration purification |
| 8 | (2-MeO)PhB(OH)$_2$ | 6.34 | trituration purification |
| 9 | (3-MeO)PhB(OH)$_2$ | 6.26 | RP-8 MPLC purification |
| 10 | (3,5-diCF$_3$)PhB(OH)$_2$ | 16.62 | trituration purification |
| 11 | (4-Et)PhB(OH)$_2$ | 12.14 | RP-8 MPLC purification |
| 12 | (4-Me)PhB(OH)$_2$ | 8.73 | RP-8 MPLC purification |
| 13 | (2,4-diCl)PhB(OH)$_2$ | 13.14 | RP-8 MPLC purification |
| 14 | (3,5-diCl)PhB(OH)$_2$ | 15.97 | RP-8 MPLC purification |
| 15 | (4-Cl)PhB(OH)$_2$ | 9.88 | RP-8 MPLC purification |
| 16 | (2-Me)PhB(OH)$_2$ | 7.86 | RP-8 MPLC purification |

55:45 CH$_3$CN/H$_2$O, 0.1% TFA, 1 mL/min, C-18 Dynamax analytical column

Examples 17–19 were prepared using the general procedure described below with the desired amine.

To a solution of the product of Example 3 (100 mg, 0.31 mmol) in DMF [dimethylformamide] (5 mL) was added BOP [benzotriazolyl-N-oxy-tris(dimethylamino)phosphonium hexafluorophosphate] (140 mg, 0.32 mmol) and DIEA [disopropylethylamine] (0.54 mL, 0.31 mmol). The mixture was stirred at ambient temperature for 18 h. A solution of an amine (0.62 mmol) in DMF (2 mL) was added to the reaction and the mixture was stirred at ambient temperature for 24 h. The DMF was removed under reduced pressure and the residue was purified by preparative reverse phase HPLC using a water-acetonitrile gradient buffered with 0.1% by volume TFA [trifluoroacetic acid]. The fractions containing product were combined and lyophilized to give a white solid. [Analytical HPLC method: Vydac C$_{18}$ column (15 cm), 15 min. gradient 95:5 to 0:100 H$_2$O, 0.1% TFA: CH$_3$CN, 0.1% TFA at flow rate of 2.0 mL/min with UV detection at 215 nm].

EXAMPLE 17

8-carboxamido-9-carboxydibenzo[2,3:5,6]bicyclo[5.2.0] nonan-4-one

Analysis for C$_{19}$H$_{15}$NO$_4$.1.0H$_2$O, 0.15CHCl$_3$: calculated: C 64.38 H 4.83 N 3.92 found: C 64.73 H 4.65 N 3.94. HPLC Rt=6.85 min., purity >99%.

EXAMPLE 18

8-piperidinocarbonyl-9-carboxydibenzo[2,3:5,6]bicyclo[5.2.0]nonan-4-one

Analysis for $C_{24}H_{23}NO_4 \cdot 0.1H_2O$: calculated: C 72.34 H 6.07 N 3.52 found: C 72.01 H 5.79 N 3.52. HPLC Rt=8.62 min., purity >99.4%.

EXAMPLE 19

8-benzylaminocarbonyl-9-carboxydibenzo[2,3:5,6]bicyclo[5.2.0]-nonan-4-one

Analysis for $C_{24}H_{23}NO_4 \cdot 0.1H_2O$: calculated: C 72.34 H 6.07 N 3.52 found: C 72.01 H 5.79 N 3.52. HPLC Rt=8.60 min., purity >99%.

What is claimed is:

1. A compound of structural Formula I:

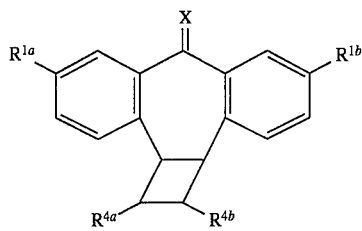

or a pharmaceutically acceptable salt thereof, wherein:

$R^{1a}$ and $R^{1b}$ groups are independently:
  (a) H, except that one and only of $R^{1a}$ and $R^{1b}$ can be hydrogen, when X is O, and $R^{4a}$ and $R^{4b}$ are both $CO_2H$,
  (b) halo(F, Cl, Br, I),
  (c) $(C_1-C_4)$ alkoxy,
  (d) $(C_1-C_5)$ alkyl,
  (e) $(C_1-C_5)$ alkylamino,
  (f) $(C_1-C_5)$ alkylthio,
  (g) $(C_1-C_5)$ perfluoroalkyl,
  (h) $SCF_3$,
  (i) $NH_2$,
  (j) $NHCOR^2$,
  (k) $NR^3COR^2$,
  (l) $COR^2$,
  (m) $NO_2$,
  (n) aryl, wherein aryl is defined as phenyl or naphthyl which is unsubstituted or substituted with substituents selected from the group consisting of: halo(F, Cl, Br, I), $(C_1-C_4)$ alkoxy, $(C_1-C_4)$ alkyl, $(C_1-C_4)$ alkylamino, $(C_1-C_4)$ alkylthio, or $(C_1-C_4)$ perfluoroalkyl, or CO-aryl, or
  (o) $CH_2$-aryl, wherein aryl is as defined above in $R^1(n)$;

$R^2$ is:
  (a) halo(F, Cl, Br, I),
  (b) $(C_1-C_4)$ alkoxy,
  (c) $(C_1-C_5)$ alkyl,
  (d) $(C_1-C_5)$ alkylamino,
  (e) aryl, wherein aryl is defined as phenyl or naphthyl, which is unsubstituted or substituted with one or two substituents selected from the group consisting of: halo(F, Cl, Br), $(C_1-C_4)$ alkoxy, $(C_1-C_4)$ alkyl, $(C_1-C_4)$ alkylamino, $(C_1-C_4)$ alkylthio, or $(C_1-C_4)$ perfluoroalkyl, or
  (f) $CH_2$-aryl, wherein aryl is as defined above in $R^2(e)$;

$R^3$ is:
  (a) $(C_1-C_5)$ alkyl,
  (b) aryl, wherein aryl is defined as phenyl or naphthyl, which is unsubstituted or substituted with one or two substituents selected from the group consisting of: halo(F, Cl, Br), $(C_1-C_4)$ alkoxy, $(C_1-C_4)$ alkyl, $(C_1-C_4)$ alkylthio, or $(C_1-C_4)$ perfluoroalkyl, or
  (c) $CH_2$-aryl, wherein aryl is as defined above in $R^3(b)$;

$R^{4a}$ and $R^{4b}$ groups are independently:
  (a) $CH_2OH$,
  (b) $CO_2H$,
  (c) $CO_2CH_3$,
  (d) $CONH_2$,
  (e) $CONHR^3$,
  (f) $CON(R^3)_2$,

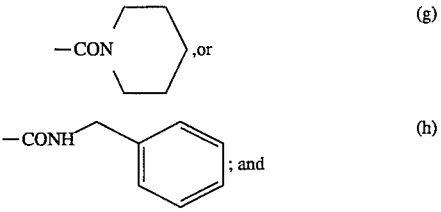

X is:
  (a) O,
  (b) H, H,
  (c) OH, H,
  (d) $OR^3$, H, or
  (e) $=CHR^3$.

2. The compound of structural formula Ia as recited in claim 1:

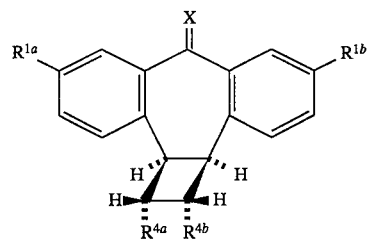

or a pharmaceutically acceptable salt thereof, wherein:

$R^{1a}$ and $R^{1b}$ groups are independently:
  (a) H, except that one and only of $R^{1a}$ and $R^{1b}$ can be hydrogen, when X is O, and $R^{4a}$ and $R^{4b}$ are both $CO_2H$,
  (b) halo(F, Cl, Br, I),
  (c) $(C_1-C_5)$ alkyl,
  (d) $(C_1-C_5)$ perfluoroalkyl,
  (e) aryl, wherein aryl is defined as phenyl or naphthyl, which is unsubstituted or substituted with substituents selected from the group consisting of: halo(F, Cl, Br, I), $(C_1-C_4)$ alkoxy, $(C_1-C_4)$ alkyl, $(C_1-C_4)$ alkylamino, $(C_1-C_4)$ alkylthio, or $(C_1-C_4)$ perfluoroalkyl, or CO-aryl, or
  (f) $CH_2$-aryl, wherein aryl is as defined above in $R^1(e)$;

$R^{4a}$ and $R^{4b}$ groups are independently:
  (a) $CH_2OH$,
  (b) $CO_2H$,
  (c) $CO_2CH_3$,
  (d) $CONH_2$,
  (e) $CONHR^3$,
  (f) $CON(R^3)_2$,

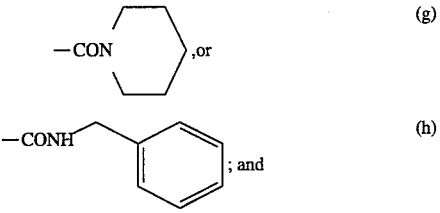

X is:
  (a) O, (b) H, H,
(c) OH, H,
(d) OR³, H, or
(e) =CHR³.

3. The compound of structural formula Ia as recited in claim 2:

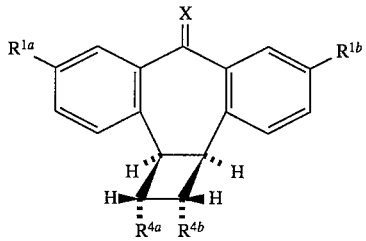

Ia or a pharmaceutically acceptable salt thereof, wherein:

$R^{1a}$ is:
(a) H, or
(b) halo(F, Cl, Br, I);

$R^{1b}$ is:
(a) H, except that one and only of $R^{1a}$ and $R^{1b}$ can be hydrogen, when X is O, and $R^{4a}$ and $R^{4b}$ are both $CO_2H$,
(b) halo(F, Cl, Br, I),
(c) ($C_1$–$C_5$) alkyl,
(d) ($C_1$–$C_5$) perfluoroalkyl,
(e) aryl, wherein aryl is defined as phenyl, 2-anisyl, 3-anisyl, 4-anisyl, 3,5-ditrifluoromethylphenyl, 2,4-ditrifluoromethylphenyl, 4-ethylphenyl, 2-tolyl, 3-tolyl, 4-tolyl, 2-chlorophenyl, 3-chlorophenyl, 4-chlorophenyl, 2,4-dichlorophenyl, 3,5-dichlorophenyl, 1-naphthyl, or 2-naphthyl, or
(f) $CH_2$-aryl, wherein aryl is as defined above in $R^1$(e);

$R^{4a}$ and $R^{4b}$ groups are independently:
(a) $CH_2OH$,
(b) $CO_2H$, or
(c) $CO_2CH_3$; and X is:
(a) O,
(b) H, H,
(c) OH, H,
(d) $OR_3$, H, or
(e) =CHR³.

4. The compound of structural formula Ia as recited in claim 3:

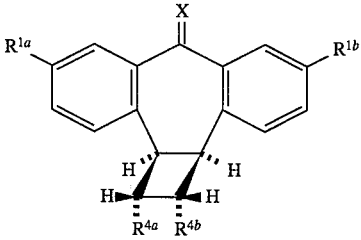

Ia wherein the substituents are as defined in the table below:

| X | $R^{1a}, R^{1b}$ | $R^{4a}, R^{4b}$ |
|---|---|---|
| O | H,1-naphthyl | $CO_2H,CO_2H$ |
| O | H,4-anisyl | $CO_2H,CO_2H$ |
| O | H,2-anisyl | $CO_2H,CO_2H$ |
| O | H,3-anisyl | $CO_2H,CO_2H$ |
| O | H,(3,5-ditrifluoromethyl)phenyl | $CO_2H,CO_2H$ |
| O | H,4-ethylphenyl | $CO_2H,CO_2H$ |

-continued

| X | $R^{1a}, R^{1b}$ | $R^{4a}, R^{4b}$ |
|---|---|---|
| O | H,4-tolyl | $CO_2H,CO_2H$ |
| O | H,(2,4-dichloro)-phenyl | $CO_2H,CO_2H$ |
| O | H,(3,5-dichloro)-phenyl | $CO_2H,CO_2H$ |
| O | H,4-chlorophenyl | $CO_2H,CO_2H$ |
| O | H,4-tolyl | $CO_2H,CO_2H$ |
| O | H,Br | $CO_2H,CO_2H$ |
| O | H,phenyl | $CO_2H,CO_2H$ |
| O | Br,Br | $CO_2H,CO_2H$ |
| H,OH | H,H | $CH_2OH,CH_2OH$. |

5. The compound of structural formula Ia as recited in claim 2:

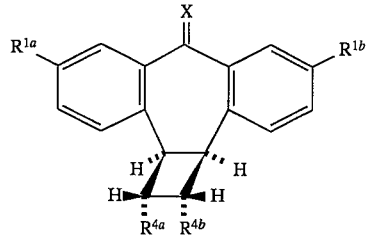

Ia or a pharmaceutically acceptable salt thereof, wherein:

$R^{1a}$ and $R^{1b}$ groups are: H;

$R^{4a}$ and $R^{4b}$ groups are independently:
(a) $CO_2H$, except that one and only of $R^{4a}$ and $R^{4b}$ can be $CO_2H$, when X is O and $R^{1a}$ and $R^{1b}$ are both hydrogen,
(b) $CONH_2$,
(c) $CONHR^3$,
(d) $CON(R^3)_2$,

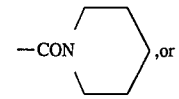

(e)

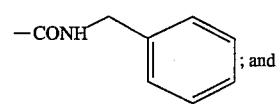

(f)

X is: O.

6. The compound of structural formula Ia as recited in claim 5:

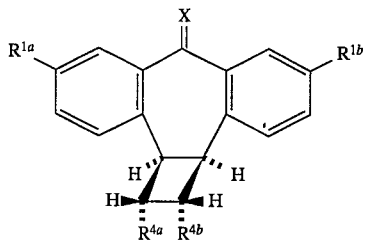

Ia wherein the substituents are as defined in the table below:

| X | $R^{1a},R^{1b}$ | $R^{4a},R^{4b}$ |
|---|---|---|
| O | H,H | $CO_2H,CONH_2$ |
| O | H,H | $CONH_2,CO_2H$ |
| O | H,H | $CO_2H$, —CON⟨⟩ |

-continued

| X | $R^{1a}, R^{1b}$ | $R^{4a}, R^{4b}$ |
|---|---|---|
| O | H,H | 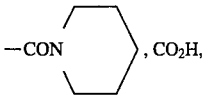 |
| O | H,H | 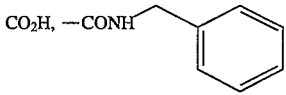 |
| O | H,H | 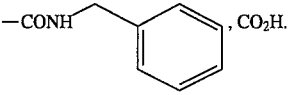 |

7. A method of treating a condition in a mammal, the treatment of which is effected or facilitated by a decrease in endothelin mediated actions, comprising the administration, in an amount that is effective for antagonizing the effect of endothelin, of a compound of Structural Formula I as recited in claim 1.

8. The method as recited in claim 7, wherein the condition is selected from the group consisting of: hypertension, pulmonary hypertension, Raynaud's disease, myocardial infarction, angina pectoris, congestive heart failure, acute renal failure, cerebral infarction, cerebral vasospasm, arteriosclerosis, vascular restenosis, asthma, inflammatory bowel diseases, endotoxic shock, endotoxin-induced multiple organ failure, disseminated intravascular coagulation, or cyclosporin-induced renal failure or hypertension.

9. The method as recited in claim 8, wherein the condition is hypertension.

10. The method as recited in claim 9, wherein the mammal is human.

11. A method of treating cardiovascular disorders by administering to a person in need of such treatment a therapeutically effective amount of a compound of Formula I as recited in claim 1.

12. The method as recited in claim 7 comprising a pharmaceutical composition of therapeutically effective amount of the compound of Formula I and a pharmaceutically acceptable carrier.

13. A pharmaceutical formulation for the treatment of hypertension comprising a pharmaceutically acceptable carrier and an effective amount of the compound of claim 1.

14. A pharmaceutical formulation for the treatment of pulmonary hypertension comprising a pharmaceutically acceptable carder and an effective amount of the compound of claim 1.

15. A pharmaceutical formulation for the treatment of asthma comprising a pharmaceutically acceptable carrier and an effective amount of the compound of claim 1.

* * * * *

UNITED STATES PATENT AND TRADEMARK OFFICE
CERTIFICATE OF CORRECTION

PATENT NO. : 5,492,917

DATED : Feb. 20, 1996

INVENTOR(S) : Ralph A. Rivero, Peter D. Williams and Daniel F. Veber

It is certified that error appears in the above-identified patent and that said Letters Patent is hereby corrected as shown below:

At Column 26, Claim 14, should read as follows:

14. A pharmaceutical formulation for the treatment of pulmonary hypertension comprising a pharmaceutically acceptable carrier and an effective amount of the compound of Claim 1.

Signed and Sealed this

Twenty-eighth Day of May, 1996

Attest:

BRUCE LEHMAN

Attesting Officer

Commissioner of Patents and Trademarks